US008221772B2

(12) United States Patent
Johnson et al.

(10) Patent No.: US 8,221,772 B2
(45) Date of Patent: Jul. 17, 2012

(54) PULMONARY SURFACTANT FORMULATIONS AND METHODS FOR PROMOTING MUCUS CLEARANCE

(75) Inventors: Mark. E. Johnson, Napa, CA (US); Robert Segal, Gwynedd Valley, PA (US); Thomas Hofmann, Doylestown, PA (US); Robert J. Capetola, Doylestown, PA (US)

(73) Assignee: Discovery Laboratories Inc., Warrington, PA (US)

( * ) Notice: Subject to any disclaimer, the term of this patent is extended or adjusted under 35 U.S.C. 154(b) by 0 days.

(21) Appl. No.: 11/901,866

(22) Filed: Sep. 19, 2007

(65) Prior Publication Data

US 2008/0199410 A1 Aug. 21, 2008

Related U.S. Application Data

(60) Provisional application No. 60/845,991, filed on Sep. 19, 2006.

(51) Int. Cl.
 *A61K 9/12* (2006.01)
 *A61K 38/03* (2006.01)
 *A61K 38/16* (2006.01)
(52) U.S. Cl. .......... 424/400; 424/450; 514/1.7; 514/1.8; 514/15.5
(58) Field of Classification Search .................. None
See application file for complete search history.

(56) References Cited

U.S. PATENT DOCUMENTS

| | | | |
|---|---|---|---|
| 4,861,756 A | 8/1989 | Jackson | |
| 4,918,161 A | 4/1990 | Steinbrink et al. | |
| 5,006,343 A | 4/1991 | Benson et al. | |
| 5,024,995 A | 6/1991 | Robertson et al. | |
| 5,164,369 A | 11/1992 | Cochrane et al. | |
| 5,223,481 A | 6/1993 | Curstedt et al. | |
| 5,238,920 A | 8/1993 | Sarin et al. | |
| 5,260,273 A | 11/1993 | Cochrane et al. | |
| 5,272,252 A | 12/1993 | McLean et al. | |
| 5,302,481 A | 4/1994 | Ong | |
| 5,407,914 A | 4/1995 | Cochrane et al. | |
| 5,455,227 A | 10/1995 | Curstedt et al. | |
| 5,508,269 A | 4/1996 | Smith et al. | |
| 5,753,621 A | 5/1998 | Dhaon et al. | |
| 5,767,068 A | 6/1998 | Van Devanter et al. | |
| 5,789,381 A | 8/1998 | Cochrane et al. | |
| 5,827,825 A | 10/1998 | Takei et al. | |
| 5,840,527 A | 11/1998 | Schilling, Jr. et al. | |
| 5,874,406 A | 2/1999 | Schafer et al. | |
| 5,891,844 A | 4/1999 | Hafner | |
| 5,925,334 A | 7/1999 | Rubin et al. | |
| 6,013,619 A | 1/2000 | Cochrane et al. | |
| 6,022,955 A | 2/2000 | Sarin et al. | |
| 6,613,734 B2 | 9/2003 | Cochrane et al. | |
| 6,660,833 B1 | 12/2003 | Walther et al. | |
| 6,926,911 B1 | 8/2005 | Boucher, Jr. | |
| 7,025,058 B2 | 4/2006 | Armstrong et al. | |
| 7,025,059 B2 | 4/2006 | Pera | |
| 2002/0037316 A1* | 3/2002 | Weers et al. | 424/450 |
| 2003/0233099 A1* | 12/2003 | Danaek et al. | 606/96 |
| 2004/0258686 A1* | 12/2004 | Chirica et al. | 424/143.1 |

FOREIGN PATENT DOCUMENTS

| | | |
|---|---|---|
| DE | 10006179 | 8/2001 |
| DE | 10006179 A1 | 8/2001 |
| EP | 0 593 094 A | 4/1994 |
| RU | 2149014 | 5/2000 |
| RU | 2198670 | 2/2003 |
| RU | 2213746 | 10/2003 |
| WO | WO/86/03408 | 6/1986 |
| WO | WO/89/04326 | 5/1989 |
| WO | WO 92/22315 A | 12/1992 |
| WO | WO 2005/025540 A2 * | 3/2005 |
| WO | WO 2005/055994 A1 * | 6/2005 |
| WO | WO 2005/115520 | 12/2005 |
| WO | WO 2006/026237 | 3/2006 |
| WO | WO 2006/055532 | 5/2006 |
| WO | WO 2006/071796 | 7/2006 |

OTHER PUBLICATIONS

Anzueto, A. et al. (1997), Effects of Aerosolized Surfactant in Patients with Stable Chronic Bronchitis: A Prospective Randomized Controlled Trial,: *J. Am. Med. Assoc.* 278:1426-1431.

Cataldo, D. et al. (2001), "Induced Sputum—Comparison Between Isotonic and Hypertonic Saline Solution Inhalation in Patients with Asthma," *Chest* 120:1815-1821.

Clark, H. and Reid, K., (2003), "The Potential of Recombinant Surfactant Protein D Therapy to Reduce Inflammation in Neonatal Chronic Lung Disease, Cystic Fibrosis, and Emphysema," *Arch. Dis. Child*, vol. 88:981-984.

Daviskas, E. et al. (2005), Inhaled Mannitol for the Treatment of Mucociliary Dysfunction in Patients with Bronchiectasis: Effect on Lung Function, Health Status and Sputum, *Respirology*, vol. 10:46-56.

Devendra, G. et al., (2002), Lung Surfactant in Subacute Pulmonary Disease,: Respir. Res. 3:19-22.

Donaldson, S. H. et al., (2006), "Mucus Clearance and Lung Function in Cystic Fibrosis with Hypertonic Saline," *N. Engl. J. Med.* 354:241-250.

Elkins, M. R. et al., (2006), "A Controlled Trial of Long-Term Inhaled Hypertonic Saline in Patients with Cystic Fibrosis," *N. Engl. J. Med.* 354:229-240.

Enhorning, G., (1977), "Pulsating Bubble Technique for Evaluating Pulmonary Surfactant," *J. Appl. Physiol.* 43:198-203.

Gibson, R. L. et al., (2003), "Pathophysiology and Management of Pulmonary Infections in Cystic Fibrosis," *Am. J. Respir. Crit. Care Med.* 168:918-951.

(Continued)

*Primary Examiner* — Jeffrey E Russel
(74) *Attorney, Agent, or Firm* — Potter Anderson & Corroon LLP

(57) ABSTRACT

Methods and compositions to enhance mucus clearance and to treat pulmonary lung disorders such as cystic fibrosis are disclosed. The methods utilize compositions including synthetic pulmonary surfactants having one or more phospholipids and a synthetic polypeptide, administered alone or combined with hyperosmotic agents, to patients in an amount effective to enhance mucus clearance.

14 Claims, 1 Drawing Sheet

OTHER PUBLICATIONS

Glasser et al., "cDNA and Deduced Amino Acid Sequence of Human Pulmonary Surfactant-Associated Proteolipid SOL(Phe)," *Proc. Natl. Acad. Sci.* 84: 4007-4011 1987.

Griese, M., (1999) "Pulmonary Surfactant in Health and Human Lung Diseases: State of the Art," *Eur. Respir. J.*, vol. 13:1455-1476.

Griese, M. et al., (1997) "Nebulization of a Bovine Surfactant in Cystic Fibrosis: A Pilot Study," *Eur. Respir. J.* 10:1989-1997.

Griese, M. et al. (2004), "Pulmonary Surfactant, Lung function, and Endobronchial Inflammation in Cystic Fibrosis," *Am. J. Respir. Crit. Care Med.*, vol. 170:1000-1005.

Griese, M. et al., (2005), "Sequential Analysis of Surfactant, Lung Function and Inflammation in Cystic Fibrosis Patients," *Respir. Res.*, vol. 6:133-142.

Hopp, T. P. et al., "Prediction of Protein Antigenic Determinants from Amino Acid Sequences," *Proc. Natl. Acad. Sci.*, vol. 78: 3824-3829, 1981.

King, R. et al., (1972), "Surface Active Materials from Dog Lung. II. Composition and Physiological Correlations," *Am. J. Physiol.*, vol. 223:715-726.

Nguyen, T. T. et al. (2003), "Generations and Characterization of Soft-Mist Aerosols From Aqueous Formulations Using the Capillary Aerosol Generator," *J. Aerosol Med.*, vol. 16:189.

Remington, *The Science and Practice of Pharmacy*, vol. II, p. 1457 (19th Ed. 1995).

Revak, S. D. et al., (1986), "Reconstitution of Surfactant Activity Using Purified Human Apoprotein and Phospholipids Measured In Vitro and In Vivo," *Am. Rev. Respir. Dis.*, vol. 134:1258-1265.

Revicki, D. A., et al., "Health-Related Quality of Life Assessment and the Pharmaceutical Industry," *Pharmacoeconomics*. Jun. 1992; 1(6):394-408.

Robertson, B., (1980), "Surfactant Substitution; Experimental Models and Clinical Applications," *Lung*, vol. 158:57-68.

Suri, R. et al., (2002), "Effects of Recombinant Human DNase and Hypertonic Saline on Airway Inflammation in Children with Cystic Fibrosis," *Am. J. Respir. Crit. Care Med.*, vol. 166:352-355.

Tierney, D. F. (1989), "Lung Surfactant: Some Historical Perspectives Leading to its Cellular and Molecular Biology," *Am. J. Physiol.*, vol. 257:L1-L12.

Zalipsky, S., "Chemistry of Polyethylene Glycol Conjugates with Biologically Active Molecules," *Adv. Drug Del. Rev.*, vol. 16: 157-82, 1995.

Zhao and Harris, "Novel Degradable Poly(ethylene Glycol) Esters for Drug Delivery," *ACS Symposium Series* 680: 458-72, 1997.

* cited by examiner

```
                        SEQUENCE LISTING

<160> NUMBER OF SEQ ID NOS: 13

<210> SEQ ID NO 1
<211> LENGTH: 21
<212> TYPE: PRT
<213> ORGANISM: Artificial Sequence
<220> FEATURE:
<223> OTHER INFORMATION: Synthetic Construct

<400> SEQUENCE: 1

Lys Leu Leu Leu Leu Lys Leu Leu Leu Leu Lys Leu Leu Leu Leu Lys
1               5                   10                  15

Leu Leu Leu Leu Lys
            20

<210> SEQ ID NO 2
<211> LENGTH: 21
<212> TYPE: PRT
<213> ORGANISM: Artificial Sequence
<220> FEATURE:
<223> OTHER INFORMATION: Synthetic Construct

<400> SEQUENCE: 2

Asp Leu Leu Leu Leu Asp Leu Leu Leu Leu Asp Leu Leu Leu Leu Asp
1               5                   10                  15

Leu Leu Leu Leu Asp
            20

<210> SEQ ID NO 3
<211> LENGTH: 21
<212> TYPE: PRT
<213> ORGANISM: Artificial Sequence
<220> FEATURE:
<223> OTHER INFORMATION: Synthetic Construct

<400> SEQUENCE: 3

Arg Leu Leu Leu Leu Arg Leu Leu Leu Leu Arg Leu Leu Leu Leu Arg
1               5                   10                  15

Leu Leu Leu Leu Arg
            20

<210> SEQ ID NO 4
<211> LENGTH: 21
<212> TYPE: PRT
<213> ORGANISM: Artificial Sequence
<220> FEATURE:
<223> OTHER INFORMATION: Synthetic Construct
```

```
<400> SEQUENCE: 4

Arg Leu Leu Leu Leu Leu Leu Leu Arg Leu Leu Leu Leu Leu Leu
1               5                   10                  15

Leu Leu Arg Leu Leu
            20

<210> SEQ ID NO 5
<211> LENGTH: 21
<212> TYPE: PRT
<213> ORGANISM: Artificial Sequence
<220> FEATURE:
<223> OTHER INFORMATION: Synthetic Construct

<400> SEQUENCE: 5

Arg Arg Leu Leu Leu Leu Leu Leu Arg Arg Leu Leu Leu Leu Leu
1               5                   10                  15

Leu Leu Arg Arg Leu
            20

<210> SEQ ID NO 6
<211> LENGTH: 20
<212> TYPE: PRT
<213> ORGANISM: Artificial Sequence
<220> FEATURE:
<223> OTHER INFORMATION: Synthetic Construct

<400> SEQUENCE: 6

Arg Leu Leu Leu Leu Cys Leu Leu Arg Leu Leu Leu Leu Leu Cys
1               5                   10                  15

Leu Leu Leu Arg
            20

<210> SEQ ID NO 7
<211> LENGTH: 21
<212> TYPE: PRT
<213> ORGANISM: Artificial Sequence
<220> FEATURE:
<223> OTHER INFORMATION: Synthetic Construct

<400> SEQUENCE: 7

Leu Leu Leu Leu Leu Cys Leu Leu Arg Leu Leu Leu Leu Cys Leu
1               5                   10                  15

Leu Leu Arg Leu Leu
            20

<210> SEQ ID NO 8
<211> LENGTH: 49
<212> TYPE: PRT
<213> ORGANISM: Artificial Sequence
<220> FEATURE:
<223> OTHER INFORMATION: Synthetic Construct

<400> SEQUENCE: 8

Arg Leu Leu Leu Leu Cys Leu Leu Arg Leu Leu Leu Leu Cys Leu
1               5                   10                  15

Leu Leu Arg Leu Leu Leu Leu Cys Leu Leu Arg Asp Leu Leu Leu
            20                  25                  30

Asp Leu Leu Leu Asp Leu Leu Leu Asp Leu Leu Leu Asp Leu Leu Leu
                35                  40                  45

Asp

<210> SEQ ID NO 9
<211> LENGTH: 19
```

```
<212> TYPE: PRT
<213> ORGANISM: Artificial Sequence
<220> FEATURE:
<223> OTHER INFORMATION: Synthetic Construct

<400> SEQUENCE: 9

Arg Leu Leu Leu Leu Cys Leu Leu Leu Arg Leu Leu Leu Leu Cys Leu
1               5                   10                  15

Leu Leu Arg

<210> SEQ ID NO 10
<211> LENGTH: 21
<212> TYPE: PRT
<213> ORGANISM: Artificial Sequence
<220> FEATURE:
<223> OTHER INFORMATION: Synthetic Construct

<400> SEQUENCE: 10

Arg Leu Leu Leu Leu Cys Leu Leu Leu Arg Leu Leu Leu Leu Cys Leu
1               5                   10                  15

Leu Leu Arg Leu Leu
            20

<210> SEQ ID NO 11
<211> LENGTH: 28
<212> TYPE: PRT
<213> ORGANISM: Artificial Sequence
<220> FEATURE:
<223> OTHER INFORMATION: Synthetic Construct

<400> SEQUENCE: 11

Arg Leu Leu Leu Leu Cys Leu Leu Leu Arg Leu Leu Leu Leu Cys Leu
1               5                   10                  15

Leu Leu Arg Leu Leu Leu Cys Leu Leu Leu Arg
            20                  25

<210> SEQ ID NO 12
<211> LENGTH: 21
<212> TYPE: PRT
<213> ORGANISM: Artificial Sequence
<220> FEATURE:
<223> OTHER INFORMATION: Synthetic Construct

<400> SEQUENCE: 12

Lys Leu Leu Leu Leu Leu Leu Leu Leu Lys Leu Leu Leu Leu Leu Leu
1               5                   10                  15

Leu Leu Lys Leu Leu
            20

<210> SEQ ID NO 13
<211> LENGTH: 21
<212> TYPE: PRT
<213> ORGANISM: Artificial Sequence
<220> FEATURE:
<223> OTHER INFORMATION: Synthetic Construct

<400> SEQUENCE: 13

Lys Lys Leu Leu Leu Leu Leu Leu Lys Lys Leu Leu Leu Leu Leu Leu
1               5                   10                  15

Leu Leu Lys Lys Leu
            20
```

PULMONARY SURFACTANT FORMULATIONS AND METHODS FOR PROMOTING MUCUS CLEARANCE

This claims benefit of U.S. Provisional Application No. 60/845,991, filed Sep. 19, 2006, the entire contents of which are incorporated by reference herein.

FIELD OF THE INVENTION

This invention relates to pharmacology. Treatments that facilitate mucus clearance in pulmonary disorders, such as cystic fibrosis, primary ciliary diskinesia, bronchiectasis, asthma and ventilator-associated pneumonia, are provided.

BACKGROUND OF THE INVENTION

Various publications, including patents, published applications, technical articles and scholarly articles are cited throughout the specification. Each of these cited publications is incorporated by reference herein, in its entirety.

Cystic fibrosis (CF) is a recessive genetic disorder with an incidence in approximately one of every 3,500 live births. CF results from a mutation in the cystic fibrosis transmembrane regulator gene, and a resultant impairment in ion transport. The result of these mutations is the secretion of abnormally thick, sticky mucus that obstructs the lungs and airways (Gibson R L et al. (2003) Am. J. Respir. Crit. Care Med. 168:918-51). Abnormalities of ion transport in the airways of CF patients lead to dehydration of airway surface liquid. Airway mucus may then become adherent to airway surfaces, eventually obstruct CF airways, and serve as a substrate for bacterial colonization and chronic infection.

In addition to CF, numerous other chronic or transient pulmonary diseases are characterized by the retention of mucous secretions in the lungs and airways. These include acute or chronic bronchitis and other chronic obstructive pulmonary disease (COPD), bronchiectasis, bronchiolitis, primary or secondary ciliary dyskinesia, asthma, sinusitis and pneumonia.

Pulmonary surfactant (PS) is important for the integrity of the lungs (Griese M et al. (2005) Am. J. Respir. Crit. Care Med. 170:1000-5). Pulmonary surfactants are synthesized by epithelial cells, and are composed of approximately 90% lipids and 10% proteins (Devendra G et al. (2002) Respir. Res. 3:19-22). PS covers the entire alveolar surface of the lungs and the terminal conducting airways leading to the alveoli, and facilitate respiration by continually modifying the surface tension of the fluid normally present within the alveoli. By lowering the surface tension of the terminal conducting airways, surfactant maintains patency, i.e., keeps airways open (Griese M (1999) Eur. Respir. J. 13:1455-76). Loss of patency leads to obstruction of the airway and compromised pulmonary function. In humans, PS primarily contains phospholipids and four surfactant polypeptides, referred to as SP-A, SP-B, SP-C and SP-D (Tierney D F et al. (1989) Am. J. Physiol. 257:L1-L12; and, Griese M (1999) Eur. Respir. J. 13:1455-76). SP-A, -B, and -C are important for lowering surface tension. In humans, the absence of SP-B is fatal. SP-A aids in resistance against inhibition of surfactant activity by inflammatory mediators and products (Griese M et al. (2005) Respir. Res. 6:133-42). SP-D facilitates phagocytosis of pathogens, and has immunomodulatory, anti-inflammatory, and antioxidative properties (Clark H et al. (2003) Arch. Dis. Child 88:981-4).

Natural and synthetic pulmonary surfactants have been studied for their potential to treat various pulmonary disorders, including asthma, bronchiolitis, chronic bronchitis, cystic fibrosis, pneumonia, and neonatal respiratory distress syndrome, among others (Griese M (1999) Eur. Respir. J. 13:1455-76). In most cases, some measurable improvement in the patients' conditions was noted, although treatment of CF patients with a bovine surfactant extract resulted in no improvement in lung function or oxygenation, due at least in part to insufficient deposition of the PS in the patients' lungs (Griese M et al. (1997) Eur. Respir. J. 10:1989-97). In contrast, treatment with aerosolized surfactant lipid palmitoylphosphadidylcholine (DPPC) was reported to improve pulmonary function and sputum transportability in patients with chronic bronchitis (Anzueto A et al. (1997), J. Am. Med. Assoc. 278:1426-1431).

Hyperosmolar solutions and aerosols have been used to promote clearance of mucous secretions from the airways, thereby improving lung function. For example, hyperosmolar dry powder mannitol was reported to improve pulmonary function in adults subjects with non-CF bronchiectasis, and to reduce the surface adhesivity and increase cough clearance of expectorated sputum (Daviskas E, et al. (2005) Respirology 10:46-56). Administration of hypertonic saline (1M) to CF patients via inhalation was reported to facilitate mucus clearance and improve lung function in the patients (see, e.g., Donaldson SH et al. (2006) N. Engl. J. Med. 354:241-50). However, the action of hypertonic saline is short-lived, and hypertonic saline by itself failed to restore the patency of many obstructed airways in the patients (Elkins M R et al. (2006) N. Engl. J. Med. 354:229-40). In addition, hypertonic saline inhalation can produce bronchoconstriction in some patients, and may potentiate inflammation (Didier C et al. (2001) Chest 120:1815-21; and, Suri R et al. (2002) Am. J. Respir. Crit. Care Med 166:352-5). As such, there is a need for therapies for CF and other such pulmonary disorders that enhance mucus clearance and lung function in patients and concomitantly restore airway patency, with limited negative side effects.

SUMMARY OF THE INVENTION

One aspect of the invention features a method for promoting mucus clearance in a patient with a pulmonary condition characterized by excessive mucus secretion, impaired mucus clearance or inflammatory pulmonary condition. The method comprises administering to the patient at least one pulmonary surfactant in an amount effective to promote mucus clearance in the patient. The pulmonary conditions treatable by the method include, but are not limited to, cystic fibrosis, acute or chronic bronchitis, bronchiectasis, bronchiolitis, primary or secondary ciliary diskinesia, COPD, asthma, pneumonia, or sinusitis.

In certain embodiments, the pulmonary surfactant is a synthetic pulmonary surfactant comprising one or more pharmaceutically acceptable phospholipids admixed with an SP-B polypeptide or fragment thereof, or a polypeptide comprising at least 10 amino acid residues and no more than about 60 amino acid residues. The polypeptide includes a sequence having alternating hydrophobic and hydrophilic amino acid residue regions represented by the formula $(ZaU_b)_cZd$, wherein Z is a hydrophilic amino acid residue independently selected from the group consisting of R and K; U is a hydrophobic amino acid residue independently selected from the group consisting of L and C; a is 1 or 2; b has an average value of about 3 to about 8; c is 1 to 10; and d is 0 to 2. In various embodiments, the pulmonary surfactant is administered as a liquid instillate, or as a liquid aerosol or a dry aerosol.

Treatment of the patient in accordance with the above-described method results in improvements that include, but are not limited to, improved airway patency, reduced inflammation, reduced airway obstruction, maintained or increased pulmonary function, and improved Health Related Quality of Life (HRQOL), relative to a patient not administered the pulmonary surfactant.

Another aspect of the invention features a method as described above, that further comprises administering an osmotically active agent to the patient. The pulmonary surfactant can be administered concomitantly or sequentially with the osmotically active agent.

The osmotically active agent can be a pharmaceutically acceptable sugar, sugar alcohol or salt. In certain embodiments, the osmotically active agent is NaCl and is formulated as a saline solution. Typically, the saline solution comprises about 0.13 to about 1.2 Osm sodium chloride.

Treatment of the patient in accordance with the above-described method also results in improvements that include, but are not limited to, improved airway patency, reduced inflammation, reduced airway obstruction, maintained or increased pulmonary function, and improved Health Related Quality of Life (HRQOL), relative to a patient not administered the pulmonary surfactant.

Another aspect of the invention features a pharmaceutical composition for promoting mucus clearance, which comprises a pulmonary surfactant and an osmotically active agent. In various embodiments, the osmotically active agent is a sugar, a sugar alcohol or a salt, and the pulmonary surfactant is a synthetic pulmonary surfactant comprising one or more pharmaceutically acceptable phospholipids admixed with an SP-B polypeptide or fragment thereof, or a polypeptide comprising at least 10 amino acid residues and no more than about 60 amino acid residues. The polypeptide includes a sequence having alternating hydrophobic and hydrophilic amino acid residue regions represented by the formula $(ZaU_b)_c Zd$, wherein Z is a hydrophilic amino acid residue independently selected from the group consisting of R and K; U is a hydrophobic amino acid residue independently selected from the group consisting of L and C; a is 1 or 2; b has an average value of about 3 to about 8; c is 1 to 10; and d is 0 to 2.

In certain embodiments, the osmotically active agent is a salt. The composition can have an osmolality between about 220-1200 mOsm/kg, a free anion concentration of between about 20-200 mmol/l and a pH between about 6.8 and 8.0.

In particular embodiments, the composition contains NaCl as the salt, and the pulmonary surfactant comprises 1,2-dipalmitoyl-sn-glycero-3-phosphocholine (DPPC), 1-palmitoyl-2-oleoyl-sn-glycero-3-phosphoglycerol (POPG), palmitic acid (PA) and a peptide having a sequence of KLLLLKLLLLKLLLLKLLLLK (KL4, SEQ ID NO:1). The composition is preferably formulated for aerosol delivery, and can be specifically formulated to deliver between about 20 and 200 mg lung dose of total phospholipid equivalent per day.

Other features and advantages of the invention will be understood by reference to the drawings, detailed description and examples that follow.

DETAILED DESCRIPTION OF ILLUSTRATIVE EMBODIMENTS

Figure 1:
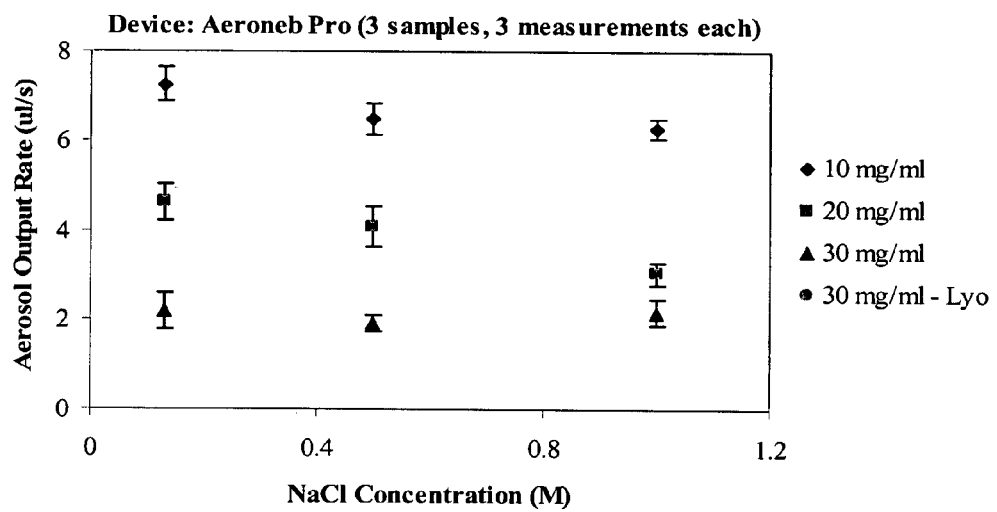
FIG. 1. Aerosol output rates (μl/sec) for lucinactant (10, 20, 30 mg/ml) or 30 mg/ml lyophilized KL4 surfactant formulations prepared with increasing concentrations of NaCl. Aerosol generator was Aeroneb Pro; data points represent three samples, three measurements each; error bars are indicated.

Various terms relating to the methods and other aspects of the present invention are used throughout the specification and claims. Such terms are to be given their ordinary meaning in the art unless otherwise indicated. Other specifically defined terms are to be construed in a manner consistent with the definition provided herein.

DEFINITIONS

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting. As used in this specification and the appended claims, the singular forms "a", "an", and "the" include plural referents unless the content clearly dictates otherwise. Thus, for example, reference to "a pulmonary surfactant" includes a combination of two or more pulmonary surfactants, and the like.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The terms "treating" or "treatment" refer to any success or indicia of success in the attenuation or amelioration of an injury, pathology or condition, including any objective or subjective parameter such as abatement, remission, diminishing of symptoms or making the injury, pathology, or condition more tolerable to the patient, slowing in the rate of degeneration or decline, making the final point of degeneration less debilitating, improving a subject's physical or mental well-being, or prolonging the length of survival. The treatment or amelioration of symptoms can be based on objective or subjective parameters; including the results of a physical examination, neurological examination, and/or psychiatric evaluations.

"Effective amount" or "therapeutically effective amount" are used interchangeably herein, and refer to an amount of a compound, formulation, material, or composition, as described herein effective to achieve a particular biological result. Such results may include, but are not limited to, the enhancement of mucus clearance, lung function, and/or airway patency, and the treatment of cystic fibrosis or other pulmonary disease in a subject, as determined by any means suitable in the art.

"Pharmaceutically acceptable" refers to those properties and/or substances which are acceptable to the patient from a pharmacological/toxicological point of view and to the manufacturing pharmaceutical chemist from a physical/ chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

"Surfactant activity" refers to the ability of any substance, such as an organic molecule, protein or polypeptide, either alone or in combination with other molecules, to lower surface tension at an air/water interface. The measurement can be made with a Wilhelmy Balance or pulsating bubble surfactometer by an in vitro assay (e.g., King et al. (1972) Am. J. Physiol. 223:715-726, and, Enhorning G (1977) J. Appl. Physiol. 43:198-203). In brief, the Enhorning Surfactometer (Surfactometer International, Toronto, Ontario) measures the pressure gradient ($\delta P$) across a liquid-air interface of a bubble that pulsates at a rate of 20 cycles/min between a maximal (0.55 mm) and minimal (0.4 mm) radius. The bubble, formed in a 37° C., water-enclosed, 20-$\mu$l sample chamber, is monitored through a microscopic optic while the pressure changes are recorded on a strip chart recorder calibrated for 0 and $-2$ cm $H_2O$. In addition, in vivo measurements of increases of compliance or airflow at a given pressure of air entering the lung can be readily made (Robertson B (1980) Lung 158:57-68). In this assay, the sample to be assessed is administered through a cannulated trachea to fetal rabbits or lambs delivered prematurely by Caesarian section. Measurements of lung compliance, blood gas tensions and ventilator pressure provide indices of activity. In vitro assays of surfactant activity, which is assessed as the ability to lower the surface tension of a pulsating bubble, and in vivo assays utilizing fetal rabbits is described in detail by Revak S D et al. (1986) Am. Rev. Respir. Dis. 134:1258-1265.

"Aerosol" refers to liquid or solid particles that are suspended in a gas. As used in the inventive methods, an aerosol contains the therapeutically active formulation. The aerosol can be in the form of a solution, suspension, emulsion, powder, solid, or semi-solid preparation.

"Osmolarity" refers to the concentration of osmotically active particles in solution expressed in terms of osmoles of solute per liter of solution. Osmolality refers to the concentration of osmotically active particles in solution expressed in terms of osmoles of solute per kilogram of solution. Osmolarity and osmolality are abbreviated "Osm" or "mOsm" herein and are distinguished on the basis of whether the measurement is made per liter or per kilogram of solution. An "osmole" is the amount of substance that dissociates in solution to form one mole of osmotically active particles.

"Osmotically active" agents used in the present invention are membrane-impermeable (i.e., essentially non-absorbable) on the airway or pulmonary epithelial surface. The terms "airway surface," "lung surface" or "pulmonary surface," as used herein, include pulmonary airway surfaces such as the bronchi and bronchioles, alveolar surfaces, and nasal and sinus surfaces. An osmotically active agent is sometimes referred to herein as an "osmolyte."

Description

Aerosolized hypertonic saline solution has been observed to improve lung function and enhance mucus clearance when administered to CF patients, although the hypertonic saline solution was not sufficient to restore patency of obstructed airways. In accordance with the present invention, pulmonary surfactant, via a detergent-like effect, is expected to help to improve mucociliary cough clearance and relieve airway obstruction by reducing mucus adhesivity. The present invention employs pulmonary surfactants, alone or combined with an osmotically active agent, to provide greater benefits in patients with pulmonary disorders characterized by abnormal mucus production, or impaired mucus clearance.

Accordingly, one aspect of the present invention features methods for the treatment of pulmonary disorders involving abnormal mucus production or impaired mucus clearance. The methods comprise administration of a pulmonary surfactant to a patient in an amount effective to promote mucus clearance in the patient. The method may optionally comprise administration of a pulmonary surfactant in conjunction with an osmotically active agent. The method may further comprise combination therapy with other mucokinetic, mucolytic or therapeutic agents.

Another aspect of the invention features pharmaceutical compositions for the treatment of pulmonary disorders involving abnormal mucus production or impaired mucus clearance. These compositions comprise a pulmonary surfactant combined with an osmotically active agent. In various embodiments, the osmolarity of the compositions is adjusted in accordance with the type of pulmonary disorder being treated, and can range from nearly isoosmotic (e.g., for treatment of sinusitis or mild forms of chronic bronchitis) to very hyperosmotic (e.g., for treatment of cystic fibrosis), as described in greater detail herein.

Methods for Promoting Mucus Clearance:

Methods are provided for promoting mucus clearance and improving lung function in patients suffering from pulmonary conditions in which mucus production is excessive, thick, or otherwise difficult to clear from the lungs and airways. Such conditions include, but are not limited to, cystic fibrosis, acute or chronic bronchitis, ventilator assisted pneumonia, bronchiectasis, bronchiolitis, primary or secondary ciliary diskinesia, COPD, asthma, pneumonia and sinusitis.

One of the methods comprises administering exogenous pulmonary surfactant (PS) to the patient, in a dosage form and regimen effective to improve mucus clearance from the lungs and airways. Without intending to be limited by mechanism, administration of PS is believed to improve mucus clearance from airways by lowering surface tension and increasing fluidity of mucosal plugs, thus facilitating mucus clearance and acting as an expectorant. Mucus may drain away from otherwise inaccessible areas of the lung and may thereby become accessible to other therapeutic agents. In addition, certain surfactants, such as lucinactant and other non-animal derived surfactants have been shown to have anti-inflammatory properties, which will be extremely beneficial in reducing the signs and symptoms of CF and other of the above-listed lung conditions in which inflammation and infection (e.g., *Pseudomonas aeruginosa*) play a role.

Another method comprises a combination therapy of PS and an osmotically active agent. Osmotically active agents, such as hyperosmotic saline, have been shown to promote clearance of mucous secretions from the airways, thereby improving lung function. However, such agents may not successfully restore airway patency, and their use can produce bronchoconstriction in some patients, and may potentiate inflammation. The administration of PS in conjunction with osmotically active agents will alleviate some of these negative side effects, while providing the additional benefits of reduced surface tension in the lungs and airways and increased mucus fluidity as described above.

Either of the foregoing methods may be combined with additional therapy for the condition being treated, including treatment with other therapeutic agents such as steroids, nitric oxide, antioxidants or reactive oxygen scavengers, corticosteroids, expectorants, mucolytic agents, bronchodilators, diuretics, antimicrobial or anti-infective agents, anti-hypertensive agents, or anti-inflammatory agents (e.g., PLA2 inhibitors, protease or elastase inhibitors, PDE-4 inhibitors, to name only a few), as would be appreciated by one of skill in the art. Such agents can be administered concurrently or sequentially with the surfactant formulations and osmotically active agents, if used. Sequential administration of additional therapeutic agents can be prior or subsequent to the administration of the hyperosmotic agent and surfactant formulation. Sequential administration can be carried out at different points in time. Thus, each component can be administered separately but sufficiently closely in time so as to provide the desired therapeutic effect. It is within the capabilities of the skilled artisan to determine the appropriate timing, sequence and dosages of administration for particular drugs of the present invention.

Pulmonary Surfactants:

Any pulmonary surfactant currently in use, or hereafter developed for use in respiratory distress system and other pulmonary conditions, is suitable for use in the present invention. These include naturally occurring and synthetic pulmonary surfactant. Synthetic PS, as used herein, refers to both protein-free lung surfactants and pulmonary surfactants comprising synthetic peptides, including peptide mimetics of naturally occurring surfactant protein. Current PS products include, but are not limited to, lucinactant (Surfaxin®, Discovery Laboratories, Inc., Warrington, Pa.), bovine lipid surfactant (BLES®, BLES Biochemicals, Inc. London, Ont), calfactant (Infasurf®, Forest Pharmaceuticals, St. Louis, Mo.), natural bovine surfactant (Alveofact®, Thomae, Germany), bovine surfactant (Surfactant TA®, Tokyo Tanabe, Japan), poractant alfa (Curosurf®, Chiesi Farmaceutici SpA, Parma, Italy), pumactant (Alec®, Britannia Pharmaceuticals, UK), beractant (Survanta®, Abbott Laboratories, Inc., Abbott Park, Ill.) and colfosceril palmitate (Exosurf®, GlaxoSmithKline, plc, Middlesex, U.K.). In a preferred embodiment, the PS comprises synthetic peptides. Among other advantages, a synthetic PS of this type is less immunogenic than naturally occurring PS or PS comprising animal-derived proteins. It is therefore more suitable for repeated exposure as would be needed for the treatment of chronic conditions.

In certain aspects, a pulmonary surfactant of the present invention comprises a cationic peptide that can be derived from animal sources or synthetically. Exemplary peptides for use herein include naturally and non-naturally occurring pulmonary surfactant polypeptides, such as, for example, one or a combination of animal-derived SP-A, SP-B, SP-C, or SP-D polypeptides; recombinant SP-A, SP-B, SP-C, or SP-D polypeptides; synthetically derived SP-A, SP-B, SP-C, or SP-D polypeptides; SP-A, SP-B, SP-C, and SP-D analogs; SP-A, SP-B, SP-C, and SP-D polypeptide mimics; conservatively modified variants thereof retaining activity; and fragments thereof retaining activity. A pulmonary surfactant polypeptide mimic is generally a polypeptide that is engineered to mimic the essential attributes of human surfactant protein. In certain preferred embodiments, the pulmonary surfactant polypeptide comprises a cationic peptide that consists of at least about 10, preferably at least 11 amino acid residues, and no more than about 80, more usually fewer than about 35 and preferably fewer than about 25 amino acid residues.

Exemplary amino acid sequences of pulmonary surfactant polypeptides for use herein, methods of isolating them, and producing them by genetic engineering techniques are known in the art. See for example, U.S. Pat. Nos. 5,874,406; 5,840,527; 4,918,161; 5,827,825; 6,660,833, 5,006,343; 5,455,227; 5,223,481; 5,753,621; 5,891,844; 4,861,756; 5,272,252; 5,024,95; 5,238,920; 5,302,481; 6,022,955; 5,874,406; 5,840,527; 5,827,825; 6,013,619; 6,660,833; and International Publication Nos. WO8603408 and WO8904326. A preferred lung surfactant peptide for use herein is a SP-B or SP-C polypeptide, or polypeptide mimic.

A preferred synthetic pulmonary surfactant comprises one or more phospholipids and a polypeptide, in which the polypeptide, when admixed with a phospholipid, forms a synthetic pulmonary surfactant having a surfactant activity greater than the surfactant activity of the phospholipid alone. A particularly preferred pulmonary surfactant polypeptide for use herein is a SP-B polypeptide or polypeptide mimic. SP-B is the protein in natural pulmonary surfactant known to be the most important surfactant protein for surface tension lowering and promoting oxygen exchange. SP-B polypeptide mimics are small hydrophobic polypeptides, generally less than about 80 amino acids in size. Many SP-B polypeptide mimics possess a repeating hydrophobic cationic motif. Like natural SP-B polypeptide, SP-B mimics, preferably, lower surface tension of the terminal conducting airways and promote oxygen exchange. Further, surfactant formulations containing such SP-B mimics (e.g., lucinactant) are believed to have antibiotic properties and are non-immunogenic.

A preferred SP-B mimetic for use in the present invention is KL4 peptide, which is a cationic peptide containing repeating lysine and leucine residues. KL4 is representative of a family of pulmonary surfactant polypeptide mimetics which are described, for example, in U.S. Pat. Nos. 5,260,273, 5,164,369, 5,407,914 and 6,613,734. Methods of preparing the KL4 peptide can be found in U.S. Pat. No. 5,164,369.

In certain embodiments, pulmonary surfactants polypeptide mimics refer to polypeptides with an amino acid residue sequence that has a composite hydrophobicity of less than zero, preferably less than or equal to $-1$, more preferably less than or equal to $-2$. The composite hydrophobicity value for a peptide is determined by assigning each amino acid residue in a peptide its corresponding hydrophilicity value as described in Hopp et al., *Proc. Natl. Acad. Sci.* 78: 3824-3829, 1981. For a given peptide, the hydrophobicity values are summed, the sum representing the composite hydrophobicity value. These hydrophobic polypeptides typically perform the function of the hydrophobic region of SP18. Accordingly, in certain embodiments, the amino acid sequence of the pulmonary surfactant polypeptide mimics the pattern of hydrophobic and hydrophilic residues of SP18 and perform the function of the hydrophobic region of SP18. SP18 is a known lung surfactant apoprotein, more thoroughly described in Glasser et al., *Proc. Natl. Acad. Sci.* 84: 4007-4001, 1987. It should be understood, however, that polypeptides and other surfactant molecules of the present invention are not limited to molecules having sequences like that of native SP18. On the contrary, some preferred surfactant molecules of the present invention have little resemblance to SP18 with respect to a specific amino acid residue sequence, except that they have similar surfactant activity and alternating charged/uncharged (or hydrophobic/hydrophilic) residue sequences.

In certain embodiments, exemplary polypeptides for use herein have alternating hydrophobic and hydrophilic amino acid residue regions and are characterized as having at least 10 amino acid residues represented by the formula:

$$(Z_a U_b)_c Z_d$$

Z and U are amino acid residues such that at each occurrence Z and U are independently selected. Z is a hydrophilic amino acid residue, preferably selected from the group consisting of R, D, E and K. U is a hydrophobic amino acid residue, preferably selected from the group consisting of V, I, L, C, Y, and F. The letters, "a," "b,", "c" and "d" are numbers which indicate the number of hydrophilic or hydrophobic residues. The letter "a" has an average value of about 1 to about 5, preferably about 1 to about 3. The letter "b" has an average value of about 3 to about 20, preferably about 3 to about 12, most preferably, about 3 to about 10. The letter "c" is 1 to 10, preferably, 2 to 10, most preferably 3 to 6. The letter "d" has an average value of about 0 to 3, preferably 1 to 2.

In certain embodiments, surfactant polypeptides include a sequence having alternating groupings of amino acid residues as represented by the formula:

$$(Z_a J_b)_c Z_d$$

wherein Z is an amino acid residue independently selected from the group consisting of R, D, E, and K; J is an α-aminoaliphatic carboxylic acid; a has an average value of about 1 to about 5; b has an average value of about 3 to about 20; c is 1 to 10; and d is 0 to 3.

In certain embodiments, polypeptides of the present invention have alternating groupings of amino acids residue regions as represented by the formula:

$$(B_a U_b)_c B_d$$

wherein B is an amino acid residue independently selected from the group consisting of H, 5-hydroxylysine, 4-hydroxyproline, and 3-hydroxyproline; and U is an amino acid residue independently selected from the group consisting of V, I, L, C, Y, and F. In one preferred variation, B is an amino acid derived from collagen and is preferably selected from the group consisting of 5-hydroxylysine, 4-hydroxyproline, and 3-hydroxyproline; a has an average value of about 1 to about 5; b has an average value of about 3 to about 20; c is 1 to 10; and d is 0 to 3.

In certain embodiments, surfactant polypeptides of the present invention include a sequence having alternating groupings of amino acid residues as represented by the formula:

$$(B_a J_b)_c B_d$$

wherein B is an amino acid residue independently selected from the group consisting of H, 5-hydroxylysine, 4-hydroxyproline, and 3-hydroxyproline; and J is an α-aminoaliphatic carboxylic acid; a has an average value of about 1 to about 5; b has an average value of about 3 to about 20; c is 1 to 10; and d is 0 to 3.

In various embodiments including "J" in the relevant formula, J is an α-aminoaliphatic carboxylic acid having four to six carbons, inclusive. In other variations, J is an α-aminoaliphatic carboxylic acid having six or more carbons, inclusive. In yet other variations, J is selected from the group consisting of α-aminobutanoic acid, α-aminopentanoic acid, α-amino-2-methylpropanoic acid, and α-aminohexanoic acid.

In certain embodiments, surfactant polypeptides of the present invention comprise a sequence having including a sequence having alternating groupings of amino acid residues as represented by the formula:

$$(Z_a U_b)_c Z_d$$

wherein Z is an amino acid residue independently selected from the group consisting of R, D, E, and K; and U is an amino acid residue independently selected from the group consisting of V, I, L, C, Y and F; from the group consisting of V, I, L, C and F; or from the group consisting of L and C; a has an average value of about 1 to about 5; b has an average value of about 3 to about 20; c is 1 to 10; and d is 0 to 3.

In the foregoing formulas, Z and U, Z and J, B and U, and B and J are amino acid residues that, at each occurrence, are independently selected. In addition, in each of the aforementioned formulae, a generally has an average value of about 1 to about 5; b generally has an average value of about 3 to about 20; c is 1 to 10; and d is 0 to 3.

In certain embodiments, Z and B are charged amino acid residues. In other preferred embodiments, Z and B are hydrophilic or positively charged amino acid residues. In one variation, Z is preferably selected from the group consisting of R, D, E and K. In a related embodiment, Z is preferably selected from the group consisting of R and K. In yet another preferred embodiment, B is selected from the group consisting of H, 5-hydroxylysine, 4-hydroxyproline, and 3-hydroxyproline. In one preferred embodiment, B is H. In another preferred embodiment, B is a collagen constituent amino acid residue and is selected from the group consisting of 5-hydroxylysine, (6-hydroxylysine), 4-hydroxyproline, and 3-hydroxyproline.

In certain embodiments, U and J are, preferably, uncharged amino acid residues. In another preferred embodiment, U and J are hydrophobic amino acid residues. In one embodiment, U is preferably selected from the group consisting of V, I, L, C, Y, and F. In another preferred embodiment, U is selected from the group consisting of V, I, L, C, and F. In yet another preferred embodiment, U is selected from the group consisting of L and C. In various preferred embodiments, U is L.

Similarly, in certain embodiments, B is an amino acid preferably selected from the group consisting of H, 5-hydroxylysine, 4-hydroxyproline, and 3-hydroxyproline. Alternatively, B can be selected from the group consisting of collagen-derived amino acids, which includes 5-hydroxylysine, 4-hydroxyproline, and 3-hydroxyproline.

In certain embodiments, charged and uncharged amino acids are selected from groups of modified amino acids. For example, in one preferred embodiment, a charged amino acid is selected from the group consisting of citrulline, homoarginine, or ornithine, to name a few examples. Similarly, in various preferred embodiments, the uncharged amino acid is selected from the group consisting of α-aminobutanoic acid, α-aminopentanoic acid, α-amino-2-methylpropanoic acid, and α-aminohexanoic acid.

In certain embodiments of the present invention, items "a", "b", "c" and "d" are numbers which indicate the number of charged or uncharged residues (or hydrophilic or hydrophobic residues). In various embodiments, "a" has an average value of about 1 to about 5, preferably about 1 to about 3, more preferably about 1 to about 2, and even more preferably, 1.

In various embodiments, "b" has an average value of about 3 to about 20, preferably about 3 to about 12, more preferably about 3 to about 10, even more preferably in the range of about 4-8. In one preferred embodiment, "b" is about 4.

In various embodiments, "c" is 1 to 10, preferably 2 to 10, more preferably in the range of 3-8 or 4-8, and even more preferably 3 to 6. In one preferred embodiment, "c" is about 4.

In various embodiments, "d" is 0 to 3 or 1 to 3. In one preferred embodiment, "d" is 0 to 2 or 1 to 2; in another preferred embodiment, "d" is 1.

By stating that an amino acid residue is independently selected, it is meant that at each occurrence, a residue from the specified group is selected. That is, when "a" is 2, for example, each of the hydrophilic residues represented by Z will be independently selected and thus can include RR, RD, RE, RK, DR, DD, DE, DK, and the like. By stating that "a" and "b" have average values, it is meant that although the number of residues within the repeating sequence (e.g., $Z_a U_b$)

can vary somewhat within the peptide sequence, the average values of "a" and "b" would be about 1 to about 5 and about 3 to about 20, respectively.

For example, using the formula $(Z_aU_b)_cZ_d$ for the peptide designated "KL8" in Table 2 below, the formula can be rewritten as $K_1L_8K_1L_8K_1L_2$, wherein the average value of "b" is six [i.e., (8+8+2)/3=6], c is three and d is zero.

Polypeptides of the present invention can also be subject to various changes, such as insertions, deletions and substitutions, either conservative or non-conservative, where such changes provide for certain advantages in their use.

Additional residues can be added at either terminus of a polypeptide of the present invention, such as for the purpose of providing a "linker" by which such a polypeptide can be conveniently affixed to a label or solid matrix, or carrier. Labels, solid matrices and carriers that can be used with the polypeptides of this invention are known in the art.

Amino acid residue linkers are usually at least one residue and can be 40 or more residues, more often 1 to 10 residues. Typical amino acid residues used for linking are tyrosine, cysteine, lysine, glutamic and aspartic acid, or the like. In addition, a polypeptide sequence of this invention can differ from the natural sequence by the sequence being modified by terminal-$NH_2$ acylation, e.g., acetylation, or thioglycolic acid amidation, terminal-carboxlyamidation, e.g., ammonia, methylamine, and the like.

In certain embodiments, exemplary SP-B polypeptide mimics that can be used in the present invention include, but are not limited to, those shown in the table below.

TABLE

Pulmonary Surfactant Mimetic Peptides

| Designation[1] | SEQ ID NO | Amino Acid Residue Sequence |
|---|---|---|
| KL4 | 1 | KLLLLKLLLLKLLLLKLLLLK |
| DL4 | 2 | DLLLLDLLLLDLLLLDLLLLD |
| RL4 | 3 | RLLLLRLLLLRLLLLRLLLLR |
| RL8 | 4 | RLLLLLLLLRLLLLLLLLRLL |
| R2L7 | 5 | RRLLLLLLLRRLLLLLLLRRL |
| | 6 | RLLLLCLLLRLLLLCLLLR |
| | 7 | LLLLLCLLLRLLLLCLLLRLL |
| | 8 | RLLLLCLLLRLLLLCLLLRLLLLCLLLR DLLLDLLLDLLLDLLLDLLLD |
| RCL1 | 9 | RLLLLCLLLRLLLLCLLLR |
| RCL2 | 10 | RLLLLCLLLRLLLLCLLLRLL |
| RCL3 | 11 | RLLLLCLLLRLLLLCLLLRLLLLCLLLR |
| KL8 | 12 | KLLLLLLLLKLLLLLLLLKLL |
| KL7 | 13 | KKLLLLLLLKKLLLLLLLKKL |

[1]The designation is an abbreviation for the indicated amino acid residue sequence.

The pulmonary surfactant typically comprises one or more lipids. In these embodiments, the surfactant composition can comprise, for example, from as little as about 0.05 to 100% weight percent lipid, so long as the resulting composition has surfactant activity. By weight percent is meant the percentage of a compound by weight in a composition by weight. Thus, a composition having 50 weight percent lipid contains, for example, 50 grams lipids per 100 grams total composition. The term "lipid" as used herein refers to a naturally occurring, synthetic or semi-synthetic (i.e., modified natural) compound which is generally amphipathic. The lipids typically comprise a hydrophilic component and a hydrophobic component. Exemplary lipids include, but are not limited, phospholipids, fatty acids, fatty alcohols, neutral fats, phosphatides, oils, glycolipids, surface-active agents (surfactants), aliphatic alcohols, waxes, terpenes and steroids. The phrase semi-synthetic (or modified natural) denotes a natural compound that has been chemically modified in some fashion. Preferably, the lipids of are fatty acids, alcohols, esters and ethers thereof, fatty amines, or combinations thereof.

Examples of phospholipids include native and/or synthetic phospholipids. Phospholipids that can be used include, but are not limited to, phosphatidylcholines, phospatidylglycerols, phosphatidylethanolamines, phosphatidylserines, phosphatidic acids, phosphatidylinositols, sphingolipids, diacylglycerides, cardiolipin, ceramides, cerebrosides and the like. Exemplary phospholipids include, but are not limited to, dipalmitoyl phosphatidylcholine (DPPC), dilauryl phosphatidylcholine (DLPC) (C12:0), dimyristoyl phosphatidylcholine (DMPC) (C14:0), distearoyl phosphatidylcholine (DSPC), diphytanoyl phosphatidylcholine, nonadecanoyl phosphatidylcholine, arachidoyl phosphatidylcholine, dioleoyl phosphatidylcholine (DOPC) (C18:1), dipalmitoleoyl phosphatidylcholine (C16:1), linoleoyl phosphatidylcholine (C18:2), myristoyl palmitoyl phosphatidylcholine (MPPC), steroyl myristoyl phosphatidylcholine (SMPC), steroyl palmitoyl phosphatidylcholine (SPPC), palmitoyloleoyl phosphatidylcholine (POPC), palmitoyl palmitooleoyl phosphatidylcholine (PPoPC), dipalmitoyl phosphatidylethanolamine (DPPE), palmitoyloleoyl phosphatidylethanolamine (POPE), dioleoylphosphatidylethanolamine (DOPE), dimyristoyl phosphatidylethanolamine (DMPE), distearoyl phosphatidylethanolamine (DSPE), dioleoyl phosphatidylglycerol (DOPG), palmitoyloleoyl phosphatidylglycerol (POPG), dipalmitoyl phosphatidylglycerol (DPPG), dimyristoyl phosphatidylglycerol (DMPG), distearoyl phosphatidylglycerol (DSPG), dimyristoylphosphatidylserine (DMPS), distearoylphosphatidylserine (DSPS), palmitoyloleoyl phosphatidylserine (POPS), soybean lecithin, egg yolk lecithin, sphingomyelin, phosphatidylinositols, diphosphatidylglycerol, phosphatidylethanolamine, phosphatidic acids, and egg phosphatidylcholine (EPC).

Examples of fatty acids and fatty alcohols include, but are not limited to, sterols, palmitic acid, cetyl alcohol, lauric acid, myristic acid, stearic acid, phytanic acid, dipamlitic acid, and the like. Preferably, the fatty acid is palmitic acid and preferably the fatty alcohol is cetyl alcohol.

Examples of fatty acid esters include, but are not limited to, methyl palmitate, ethyl palmitate, isopropyl palmitate, cholesteryl palmitate, palmityl palmitate sodium palmitate, potassium palmitate, tripalmitin, and the like.

An example of a semi-synthetic or modified natural lipid is any one of the lipids described above which has been chemically modified. The chemical modification can include a number of modifications; however, a preferred modification is the conjugation of one or more polyethylene glycol (PEG) groups to desired portions of the lipid. Polyethylene glycol (PEG) has been widely used in biomaterials, biotechnology and medicine primarily because PEG is a biocompatible, nontoxic, nonimmunogenic and water-soluble polymer (Zhao and Harris, *ACS Symposium Series* 680: 458-72, 1997). In the area of drug delivery, PEG derivatives have been widely used in covalent attachment (i.e., "PEGylation") to proteins to reduce immunogenicity, proteolysis and kidney clearance and to enhance solubility (Zalipsky, *Adv. Drug Del. Rev.* 16: 157-82, 1995).

Lipids that have been conjugated with PEG are referred to herein as "PEG-lipids." Preferably, when PEG-lipids are used, they are present in alcohols and/or aldehydes.

The pulmonary surfactant can comprise other excipients, including, but not limited to, various sugars such as dextrose, fructose, lactose, maltose, mannitol, sucrose, sorbitol, trehalose, and the like, surfactants such as, for example, polysorbate-80, polysorbate-20, sorbitan trioleate, tyloxapol and the like, polymers such as PEG, dextran and the like, salts such as NaCl, $CaCl_2$ and the like, alcohols, such as cetyl alcohol, and buffers.

Exemplary surfactant compositions can be prepared using methods known in the art. For example, in certain embodiments, an exemplary surfactant composition comprising lipids and polypeptides can be prepared by admixing a solution of a surfactant polypeptide with a suspension of liposomes, or by admixing the surfactant polypeptide with a suspension of liposomes, or by admixing the surfactant polypeptide and phospholipids directly in the presence of organic solvent.

Preferably, the pulmonary surfactant comprises phospholipids and free fatty acids or fatty alcohols, e.g., DPPC (dipalmitoyl phosphatidylcholine), POPG (palmitoyl-oleyl phosphatidylglycerol) and palmitic acid (PA) (see, for example, U.S. Pat. No. 5,789,381).

In certain preferred embodiments, the pulmonary surfactant is lucinactant or another pulmonary surfactant formulation comprising the synthetic surfactant protein KLLLLKLLLLKLLLLKLLLL (KL4; SEQ ID NO:1). Lucinactant, is a combination of DPPC, POPG, palmitic acid (PA) and the KL4 peptide (weight ratio of approximately 7.5:2.5: 1.35:0.267). In certain embodiments, the drug product is formulated at concentrations of, for example, 5, 10, 15, 20, 25 or 30 mg/ml of phospholipid content. In certain other embodiments, the drug product is formulated at greater concentrations, e.g., 40, 50, 60, 70, 80, 90, 100, 110, 120 or more mg/ml phospholipid content, with concomitant increases in KL4 concentration.

In other embodiments, the pulmonary surfactant is formulated for delivery as an aerosol. Examples of suitable formulations for aerosol delivery are found in WO 2006/071796. It is additionally advantageous in certain cases to utilize a lyophilized pulmonary surfactant, which may be reconstituted into a suitable pharmaceutical medium. Examples of such formulations and their methods of manufacture are found in WO 2006/055532.

Osmotically Active Agents:

Any pharmaceutically acceptable osmotically active agent that is compatible with the pulmonary surfactants described herein is considered suitable for use in the present invention. A wide variety of such agents are known in the art (see, e.g., U.S. Pat. No. 6,926,911), including ionic osmolytes such as salts, or may be non-ionic osmolytes such as sugars, sugar alcohols, and organic osmolytes. Osmolality is typically adjusted to 300 mOsm/kg, but up to 1200 mOsm/kg may be useful and is well tolerated.

Suitable ionic osmolytes include any salt consisting of a pharmaceutically acceptable anion and a pharmaceutically acceptable cation. Such compounds include but are not limited to anions and cations that are contained in FDA approved commercially marketed salts, see, e.g., Remington: The Science and Practice of Pharmacy, Vol. II, pg. 1457 (19th Ed. 1995), and can be used in any combination including their conventional combinations. Examples of suitable salts include, but are not limited to, potassium chloride, choline chloride, choline iodide, lithium chloride, meglumine chloride, L-lysine chloride, D-lysine chloride, ammonium chloride, potassium sulfate, potassium nitrate, potassium gluconate, potassium iodide, ferric chloride, ferrous chloride and potassium bromide, to name a few.

Sugars and sugar-alcohols suitable for use in the present invention include but are not limited to glycerol, dihydroxyacetone, erythrose, threose, and erythrulose, ribose, arabinose, xylose, fructose, sorbose, and tagatose), glucose, mannose, galactose, raffinose, raffinose, stachyose, sorbitol, mannitol, dulcitol, arabitol. When appropriate, both the D and L forms of each sugar or sugar alcohol are contemplated for use in the invention.

Organic osmolytes suitable for use in the present invention include but are not limited to (1) polyols (polyhydric alcohols), such as inositol, myo-inositol, and sorbitol; (2) methylamines, such as choline, betaine, carnitine (L-, D- and DL forms), phosphorylcholine, lyso-phosphorylcholine, glycerophosphorylcholine, creatine, and creatine phosphate; and (3) amino acids, such as the D- and L forms of glycine, alanine, glutamine, glutamate, aspartate, proline and taurine.

In some preferred embodiments, the osmotically active agent is a sodium salt. The anion of the sodium salt can be any suitable anion, including without limitation, acetate, citrate, lactate, carbonate, bicarbonate, phosphate, iodide, fluoride, or bromide, and is preferably chloride. The sodium salt can be monobasic or dibasic. The osmotically active agent in solution form can range from about pH 5 to about pH 9, and is preferably between about pH 6 and about pH8.

Administration:

The pulmonary surfactants, alone or combined with osmotically active agents, are administered to a patient by pulmonary delivery, e.g., in solid or liquid particulate form by inhalation into the respiratory system. Administration by inhalation can be by means of a metered dose inhaler (MDI). Metered dose inhalers release a discrete quantity of medication from a storage container. Release of the medication is achieved by using a chemical propellant to push a medication out of a storage canister (pMDI), or by using the force of inhalation to draw the medication from a holding chamber. Metered dose inhalers can release the medication when the patient depresses the storage canister, or directly inhales the medication. Administration by inhalation can be by means of a form of MDI called a dry powder inhaler (DPI). Release of the medication is achieved by using the force of inhalation to draw the medication from a holding chamber.

Preferably, administration is accomplished by means of a nebulizer (aerosol generator). In one embodiment, the aerosol generator is an ultrasonic nebulizer or vibrating membrane nebulizer or vibrating screen nebulizer. Jet nebulizers can also be employed, as the present methods can be adapted to all types of nebulizers or atomizers. In one embodiment, the aerosol generator is an Aeroneb® Professional Nebulizer (Aerogen Inc., Mountain View, Calif., USA). Alternatively, the Pari eFlow (Pari, Richmond, Va.) or Akita 1 or 2 (Activaero, Germany) may be utilized. In another embodiment, the aerosol generator is a capillary aerosol generator, an example of which is the soft-mist generator available from Chrysalis Technologies, Richmond, Va. (Nguyen T T et al. (2003) J. Aerosol Med. 16:189).

It is preferred that the methods of the invention employ the use of high output inhalers to administer the pulmonary surfactant and osmotically active agent to a patient. These include hand-held and tabletop devices that yield more than about 0.5 ml/min output rate and greater than about 15% lung deposition (e.g., Aeroneb, Pari eFlow, Chrysalis and Activaero devices as mentioned above), to ensure sufficient deposition the surfactant and other active agents into the airways in order to promote mucus clearance.

In other embodiments, an aerosolized pulmonary surfactant can be administered as provided in WO 2005/115520 and WO 2006/026237. Administration can be in conjunction with another noninvasive pulmonary respiratory therapy involving the administration of positive airway pressure. The term "noninvasive pulmonary respiratory therapy" refers to respiratory therapy that does not require endotracheal intubation, and can include continuous positive airway pressure (CPAP), bilevel positive airway pressure (BiPAP), synchronized intermittent mandatory ventilation (SIMV), and the like. The employment of such therapies involves the use of various respiratory gases, as would be appreciated by the skilled artisan. Respiratory gases used for noninvasive pulmonary respiratory therapy are sometimes referred to herein as "CPAP gas," "CPAP air," "nCPAP", "ventilation gas," "ventilation air," or simply "air." However, those terms are intended to include any type of gas normally used for noninvasive pulmonary respiratory therapy, including but not limited to gases and gaseous combinations listed above for use as the conditioning gas. In certain embodiments, the gas used for noninvasive pulmonary respiratory therapy is the same as the conditioning gas. In other embodiments, the respective gases are different from one another.

In certain embodiments, the pulmonary delivery methods of this invention are employed in conjunction with CPAP. It has been shown that use of CPAP allows for an increase in functional residual capacity and improved oxygenation. The larynx is dilated and supraglottic airway resistance is normal. There is also an improvement of the synchrony of respiratory thoracoabdominal movements and enhanced Hering-Breuer inflation reflex following airway occlusion. CPAP has been shown to be useful in treating various conditions such as sleep apnea, snoring, ARDS, IRDS, and the like.

CPAP requires a pressure source and a delivery device or delivery apparatus. CPAP-producing airflow is typically generated in the vicinity of the nasal airways by converting kinetic energy from a jet of fresh humidified gas into a positive airway pressure. A continuous flow rate of breathing gas of about 5 to about 12 liters/minute generates a corresponding CPAP of about 2 to about 10 cm $H_2O$. Various modifications can be applied to the CPAP system which include sensors that can individualize the amount of pressure based on the patient's need.

Typically, flow rates and pressures suitable for achieving CPAP are based upon the characteristics of the patient being treated. Suitable flow rates and pressures can be readily calculated by the attending clinician. The present invention encompasses the use of a variety of flow rates for the ventilating gas, including low, moderate and high flow rates. In certain embodiments, the aerosol can be supplied during rapid, or high frequency, alterations in flow and/or pressure. High frequency is typically characterized as 0.5 hertz and above. Alternatively, the aerosol can be supplied without added positive pressure, i.e., without CPAP as a simultaneous respiratory therapy. In certain embodiments, the aerosol can be supplied during rapid, or high frequency, oscillatory percussion to the thorax.

Preferably, the CPAP-generating air flow being delivered to the patient has a moisture level which will prevent unacceptable levels of drying of the lungs and airways. Thus, the CPAP-generating air is often humidified by bubbling through a hydrator, or the like to achieve a relative humidity of preferably greater that about 70%. More preferably, the humidity is greater than about 85% and still more preferably 98%.

A suitable source of CPAP-inducing airflow is the underwater tube CPAP (underwater expiratory resistance) unit. This is commonly referred to as a "bubble" CPAP. Another preferred source of pressure is an expiratory flow valve that uses variable resistance valves on the expiratory limb of CPAP circuits. This is typically accomplished via a ventilator. Another preferred source is the Infant Flow Driver or "IFD" (Electro Medical Equipment, Ltd., Brighton, Sussex, UK). IFD generates pressure at the nasal level and employs a conventional flow source and a manometer to generate a high pressure supply jet capable of producing a CPAP effect. It is suggested in the literature that the direction of the high pressure supply jet responds to pressures exerted in the nasal cavity by the patient's efforts and this reduces variations in air pressure during the inspiration cycle. Other CPAP systems including those that contain similar features to systems just discussed are also contemplated by the present invention.

The aerosol stream generated in accordance aerosolized delivery is preferably delivered to the patient via a nasal delivery device which can involve, for example masks, single nasal prongs, binasal prongs, nasopharyngeal prongs, nasal cannulae and the like. The delivery device is chosen so as to minimize trauma, maintain a seal to avoid waste of aerosol, and minimize the work the patient must perform to breathe.

When used as an aerosol preparation, the surfactant formulation, with or without an osmotically active agent, can be supplied in finely divided form, optionally in combination with a suitable propellant. Useful propellants are typically gases at ambient conditions and are condensed under pressure including, for example, lower alkanes and fluorinated alkanes, such as freon. In certain embodiments wherein the surfactant composition is delivered as an aerosol, the aerosol can be packaged in a suitable container under pressure.

The osmotically active agents and surfactant formulations can also be administered as a dry aerosol. Such formulations are administered by the patient inhaling an aerosolized powder formulation. For example, a powder formulation may be presented in unit dosage form such as a capsule or cartridge, and administered as in U.S. Pat. No. 7,025,059 or 7,025,058.

Solid or liquid particulate forms of the formulations prepared for practicing the methods of the present invention include particles of respirable size, that is, particles of a size sufficiently small to pass through the nasal passage, mouth and trachea upon inhalation and ultimately into the bronchi and alveoli of the lungs. In general, particles ranging from about 1 to 10 microns in size, and about 3-6 microns (GSD of <2) for lung delivery, are within the respirable range. In certain embodiments, the average particle size is at least about 1, or at least about 2, or at least about 3, or at least about 4, or at least about 5, or at least about 6 microns in diameter. In other embodiments, the particle size is less than about 6, or less than about 7, or less than about 8, or less than about 9, or less than about 10 microns in diameter. Because aerosolized particles too large to be respirable can be deposited in the throat and swallowed, it is preferable that the quantity of non-respirable particles in the aerosol be as low as possible. Delivery of aerosolized therapeutics, particularly aerosolized antibiotics, is known in the art (see, e.g., U.S. Pat. Nos. 7,025,058, 7,025,059, 5,767,068, and 5,508,269.

The administration of pulmonary surfactant as a liquid instillate or an aerosol can also be carried out while the patient is being supported by invasive mechanical ventilation. The pulmonary surfactant can be administered via an oral pathway, such as an endotracheal tube, via an artificial pathway, such as a tracheostomy tube, or via a nasal pathway, using a nasal mask, prongs, cannulae, and the like. In one embodiment, the surfactant formulation is delivered via an endotracheal or tracheostomy tube that is also utilized to administer the invasive mechanical ventilation. In other embodiments, the surfactant formulation can be delivered via the mode of delivery that is utilized to administer noninvasive mechanical ventilation.

Therapeutically Effective Amounts:

To treat a patient afflicted with a pulmonary disorder involving excessive mucus production or impaired mucus clearance, a therapeutically effective amount of a pulmonary surfactant, alone or combined with an osmotically active agent, is administered to the subject. A therapeutically effective amount will provide a clinically significant enhancement of mucus clearance, improvement in lung function, and/or an improvement in airway patency, and preferably will not facilitate or sustain an inflammatory response or bronchoconstriction.

A therapeutically effective amount may be dependent on any number of variables, including without limitation, the sex, size, height, weight, age, overall health of the subject, the type of formulation, the mode or manner of administration, or the severity of the pulmonary disorder. The appropriate effective amount can be routinely determined by those of skill in the art using routine optimization techniques and the skilled and informed judgment of the practitioner and other factors evident to those skilled in the art. Preferably, a therapeutically effective dose of the osmotically active agents and surfactant formulations described herein will provide therapeutic benefit without causing substantial toxicity to the subject.

Toxicity and therapeutic efficacy of agents or compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Agents or compositions that exhibit large therapeutic indices are preferred. The dosage of such agents or compositions lies preferably within a range of circulating concentrations that include the $ED_{50}$ with little or no toxicity. The dosage may vary within this range depending upon the dosage form employed and the route of administration utilized.

In the inventive methods, at least one pulmonary surfactant is administered to a patient. A single surfactant dose ranges from, for example, about 20 to about 300 mg total phospholipidid (TPL)/kg of the patient, more preferably from about 60 to about 175 mg TPL/kg. In certain embodiments, the single surfactant dose is at least about 20, or 30, or 40, or 50, or 60 TPL/kg. In certain embodiments, the single surfactant dose is up to about 70, or 80, or 90, or 100, or 110, or 120, or 130, or 140, or 150, or 160, or 170, or 180, or 190, or 200, or 210, or 220, or 230, or 240, or 250, or 260, or 270, or 280, or 290, or 300 TPL/kg. It is understood, of course, that the exact dose of surfactant will depend upon factors such as the sex, size, height, weight, age, overall health of the subject, the type of formulation, the mode or manner or administration, or the severity of the pulmonary disorder age, as well as other factors within the knowledge or skill of the attending clinician. In certain embodiments wherein the surfactant composition is delivered as an aerosol, such as disclosed in WO 2005/115520 and WO 2006/026237, the effective dose of lung surfactant can be, for example, from about 1 mg TPL/kg surfactant to about 1000 mg TPL/kg surfactant. In certain embodiments, the effective dose of lung surfactant is about 2 mg TPL/kg or more surfactant, In certain embodiments, the effective dose is up to about 175 mg TPL/kg surfactant. In other embodiments, the effective dose of lung surfactant is up to about 200, up to about 300, up to about 400, up to about 500, up to about 600, up to about 700, up to about 800, up to about 900 or up to about 1,000 mg TPL/kg. In certain embodiments wherein the surfactant composition is delivered as a dry powder formulation, the effective dose of lung surfactant can be, for example, from about 1 mg TPL/kg surfactant to about 1000 mg or more TPL/kg surfactant, preferably from about 2 mg TPL/kg surfactant to about 175 mg TPL/kg surfactant. Other methods of delivery include lavage, lung wash, and the like. When so employed, dose ranges are well within the skill of one in the art. In certain embodiments, doses are adjusted to provide the patient with about 20 mg or more, or 30 mg or more lung dose of TPL per day, up to about 150 mg, 160 mg, 170 mg, 180 mg, 190 mg or 200 mg lung dose of TPL per day, for instance, ranging from about 20-200 mg lung dose of TPL per day, more specifically about 30-150 mg lung dose of TPL per day, and yet more specifically about 60 mg lung dose of TPL per day. Optimally, the surfactant is not animal-derived, non-immunogenic and includes the KL4 peptide.

In other embodiments, an osmotically active agent and at least one surfactant as exemplified herein is administered to a patient. The osmolality of the buffer can be at least about 100, 150, 200, 250, 300, 350, 400, 450, 500, 550, 600, 650, 700, 750, 800, 850 or 900 mOsm/kg. It can range up to about 300, 350, 400, 450, 500, 550, 600, 650, 700, 750, 800, 850, 900 950, 1,000, 1,050, 1,100, 1,150, 1,200, 1,250, 1,300, 1,350, 1,400, 1,450 or 1,500 mOsm/kg. In certain embodiments, the osmolality of the buffer can range from about 100 mOsm/kg to about 1500 mOsm/kg. More specifically, the osmolality of the buffer ranges from about 150-1000 mOsm/kg, more specifically from about 200-800 mOsm/kg, and even more specifically from about 250-300 mOsm/kg.

Treatment can be initiated with smaller dosages that are less than the optimum dose of the osmotically active agent and/or surfactant formulation, followed by an increase in dosage over the course of the treatment until the optimum effect under the circumstances is reached. If needed, the total daily dosage may be divided and administered in portions throughout the day. In combination therapy, various regimens may be advantageous, depending on the nature and severity of the pulmonary condition. For example, the pulmonary surfactant and the osmotically active agent may be administered together, and indeed may be included in the same pharmaceutical composition, as described in greater detail below. Alternatively, the surfactant and the osmotically active agent may be administered in succession. In another embodiment, a regimen may comprise alternating treatments of pulmonary surfactant and osmotically active agent.

For effective treatment of pulmonary disorders, one skilled in the art may recommend a dosage schedule and dosage amount adequate for the subject being treated. It may be preferred that dosing occur one to ten times daily, or more, for as long as needed. The dosage schedule may also vary depending on the form of administration (e.g., dry aerosol, liquid instillate, or liquid aerosol), or upon the individual needs of the subject. Administration is continued for a period of time deemed by a physician or other medical practitioner as appropriate to achieve a therapeutic or prophylactic effect. Treatment can be continued, for example, for one or more weeks, one or more months, or one or more years, including the lifetime of the patient.

In an exemplary embodiment, a synthetic pulmonary surfactant having a formulation similar to that of lucinactant (containing KL4 peptide) is utilized, adapted for aerosolization as needed, for example by adjusting phospholipid content and ratio, dilution of starting material and the like. KL4 surfactant, when aerosolized at a dose from about 5 to 30 mg/ml, is preferably administered from an efficient drug-nebulizer system, as described above. For instance, 5-7 ml of 20 mg/ml lucinactant may be delivered via a vibrating mesh nebulizer (eFlow, Aeroneb) three times daily. Alternatively, 3 ml of 20 mg/ml lucinactant may be delivered using an Akita II inhalation system (Activaero GmbH, Wohraer Str. 37 D-35285 Gemunden/Wohra, Germany) three times daily.

In any of the dosing regimens mentioned above, the skilled clinician will evaluate clinical parameters such as improvements in airway patency, lung function, e.g., $FEV_1$ and other common tests, mucociliary clearance and Health Related Quality of Life (HRQOL; see, e.g., Revicki D A, et al., Pharmacoeconomics. 1992 June; 1(6):394-408) after a period of treatment, e.g., 7, 14, 21, 28 days, to determine the efficacy of the treatment.

Pharmaceutical Compositions:

Another aspect of the invention features compositions comprising an osmotically active agent and at least one pulmonary surfactant in an amount effective to treat pulmonary disorders characterized by excess mucus secretion or impaired mucus clearance. These pharmaceutical compositions may comprise any combination of pulmonary surfactant and osmotically active agent as described above, as long as the respective components are not chemically, physically or biologically incompatible with one another. The pharmaceutical compositions may also comprise additional therapeutic agents or other components, consistent with those set forth above. Also as described above for individual components, the pharmaceutical compositions may be formulated for delivery as liquid instillates, liquid aerosols or dry aerosols.

In a preferred embodiment, the pulmonary surfactant is lucinactant or a similar formulation comprising a mixture of phospholipids and a synthetic polypeptide mimetic of SP-B, such as KL4, and the osmotically active agent is a salt, such as sodium chloride. In certain embodiments, the osmolality of the composition may range from about 220-800 mOsm/kg, or more specifically, from about 250-300 mOsm/kg. In specific situations, such as in the treatment of cystic fibrosis, the osmolality employed may be up to 900-1200 or more mOsm/kg. Thus, in certain embodiments, the osmolality of the composition is greater than about 200, or greater than about 210, or greater than about 220, or greater than about 230, or greater than about 240, or greater than about 250, or greater than about 260, or greater than about 270, or greater than about 280, or greater than about 290, or greater than about 300, or greater than about 310, or greater than about 320, or greater than about 330, or greater than about 340, or greater than about 350, or greater than about 360, or greater than about 370, or greater than about 380, or greater than about 390, or greater than about 400 mOsm/kg. In certain embodiments, the osmolality of the composition may be up to 300, or 310, or 320, or 330, or 340, or 350, or 360, or 370, or 380, or 390, or 400, or 410, or 420, or 430, or 440, or 450, or 460, or 470, or 480, or 490, or 500, or 510, or 520, or 530, or 540, or 550, or 560, or 570, or 580, or 590, or 600, or 610, or 620, or 630, or 640, or 650, or 660, or 670, or 680, or 690, or 700, or 710, or 720, or 730, or 740, or 750, or 760, or 770, or 780, or 790, or 800, or 850, or 900, or 950, or 1,000, or 1,050, or 1,100, or 1,150, or 1,200 mOsm/kg. The free anion content of the composition may range from about 20-200 mmol/l or, more specifically, from about 20-50 mmol/l. In certain embodiments, the free anion content of the composition is at least about 20, or 30, or 40, or 50 mmol/l. In other embodiments, the free anion content of the compositions is up to about 40, or 50, or 60, or 70, or 80, or 90, or 100, or 110, or 120, or 130, or 140, or 150, or 160, or 170, or 180, or 190, or 200 mmol/l. The pH of the compositions typically are at least about 6.8. The pH may range up to about 7.4, or 7.5, or 7.6, or 7.7, or 7.8, or 7.9, or 8.0. In particular embodiments, the pH may range from about 6.8-8.0 or, more specifically, from about 6.8-7.4. The concentration of surfactant in the composition typically is at least about 5, or 10, or 15, or 20, or 25, or 30 mg/ml. The concentration of surfactant in the composition may be up to about 10, or 20, or 30, or 40, or 50, or 60 or more mg/ml. In certain embodiments, the concentration of surfactant in the composition can range from, e.g., about 5-60 mg/ml, more specifically about 10-30 mg/ml, even more specifically about 15-20 mg/ml, with this latter dilution being particularly applicable to aerosol formulations. It will be appreciated that the surfactant concentration and/or osmolality of the pharmaceutical composition may be adjusted in accordance with the nature and severity of the pulmonary condition being treated. For example, treatment of mild chronic bronchitis may require a composition with osmolality in the range of, e.g., 300-500 mOsm/kg, while treatment of cystic fibrosis would utilize a composition with osmolality in the range of, e.g., 400-1200 mOsm/kg. To reduce the side effects associated with extremely hyperosmotic treatment, the concentration of pulmonary surfactant may also need to be increased. A pre-treatment with a bronchodilator medication, such as an inhaled beta-agonist (e.g., albuterol), may also be useful to assure optimal lung deposition of the aerosolized surfactant.

Pharmaceutical compositions comprising a pulmonary surfactant and an osmotically active agent are prepared in accordance with standard pharmaceutical methodology. For example, formulations can be made as liquid dispersions by a wide variety of methods, including the thin film evaporator technique, or as lyophilized product. The osmotic agent can be included in the surfactant during manufacturing. Alternatively, it can be combined with the surfactant at the time of use, e.g., by either diluting a liquid dispersion or reconstituting a lyophilized product with a solution containing the osmotic agent. Additionally, a dry osmotic agent can be added to the liquid surfactant (either liquid dispersion or reconstituted lyophilized product) at the time of use.

The following examples are provided to describe the invention in more detail. They are intended to illustrate, not to limit the invention.

Example 1

Determination of High Molar Salt Effect on Surfactant Formulation Viscosity

Increasing concentrations of NaCl were added to pulmonary surfactant-containing solutions as described in Table 1. The buffer used in these examples was Tris (Tris Hydroxymethylaminoethane; Trisamine). In the table, "dispersion" refers to formulation prepared as i) a liquid dispersion and "lyo: refers to a formulation that was produced as a lyophilized product and then reconstituted at the time of use.

TABLE 1

Surfactant-salt solution formulations.

| Formulation | Total Phospholipid Concentration (mg/ml) | Buffer Concentration (M) | n |
|---|---|---|---|
| S-43 | 10 | 0.13 | 3 |
| S-43 | 10 | 0.5 | 3 |
| S-43 | 10 | 1.0 | 3 |
| S-43 | 20 | 0.13 | 3 |
| S-43 | 20 | 0.5 | 3 |

TABLE 1-continued

Surfactant-salt solution formulations.

| Formulation | Total Phospholipid Concentration (mg/ml) | Buffer Concentration (M) | n |
|---|---|---|---|
| S-43 | 20 | 1.0 | 3 |
| Dispersion | 30 | 0.13 | 3 |
| Dispersion | 30 | 0.5 | 3 |
| Dispersion | 30 | 1.0 | 3 |
| Lyo | 30 | 0.13 | 3 |
| Lyo | 30 | 0.5 | 3 |
| Lyo | 30 | 1.0 | 3 |

Each formulation was then evaluated for its apparent viscosity at 25° C. The apparent viscosities of the surfactant formulations were measured over at 25° C. using a TA AR1000 Rheometer (TA Instruments, New Castle, Del., USA) fitted with a 40 mm/1° acrylic cone. The surfactant formulations were removed from the refrigerator and allowed to equilibrate at room temperature for 30 min. Approximately 350 µl of undiluted surfactant was placed on the rheometer and allowed to thermally equilibrate with the set temperature. The samples were analyzed in a step flow procedure with a linear increase in the shear rate with time (0 to 200 sec-1) followed by linear decrease in shear rate (200 to 0 sec$^{-1}$) over approximately 6 min of total run time. Apparent viscosity values measured at a shear rate of 157 sec-1 during the ramp up and ramp down were averaged and reported. Each surfactant formulation was analyzed in triplicate at each temperature.

The results of the viscosity measurements are set forth in Table 2. The results demonstrate no discernable impact of NaCl concentration on the apparent viscosity of the sample.

TABLE 2

Apparent viscosity of salt-surfactant formulations at 25° C.

| NaCl Conc. (M) | Apparent Viscosity at 25° C. (cp) (n = 3) | | | | | | | |
|---|---|---|---|---|---|---|---|---|
| | 10 mg/ml | | 20 mg/ml | | 30 mg/ml | | 30 mg/ml - Lyo | |
| | Avg | SD | Avg | SD | Avg | SD | Avg | SD |
| 0.13 | 9 | 1 | 28 | 1 | 43 | 5 | 12 | 1 |
| 0.5 | 9 | 1 | 29 | 1 | 32 | 7 | 9 | 1 |
| 1.0 | 9 | 0 | 28 | 2 | 31 | 9 | 7 | 1 |

Example 2

Determination of Surfactant-Salt Formulation Activity In Vitro

Each surfactant-salt solution was evaluated to determine its surface activity in vitro. Samples were diluted in 20 mM Tris-Ac/130 mM NaCl buffer at pH 7.6, or a matching buffer: 20 mM Tris-Ac pH 7.6 containing 0.13, 0.5, or 1.0M NaCl. The results of the in vitro activity measurements are set forth in Tables 3 (20 mM Tris-Ac/130 mM NaCl) and 4 (matching buffer). No impact of NaCl concentration on in vitro activity of the samples when diluted using 0.13 NaCl buffer was observed.

TABLE 3

Activity of samples diluted in 20 mM Tris-Ac/130 mM NaCl buffer.

| NaCl Conc. (M) | Minimum Surface Tension at 3 mg-TPL/ml (mN/m)(n = 3) | | | | | | | |
|---|---|---|---|---|---|---|---|---|
| | 10 mg/ml | | 20 mg/ml | | 30 mg/ml | | 30 mg/ml - Lyo | |
| | Avg | SD | Avg | SD | Avg | SD | Avg | SD |
| 0.13 | 0 | 0 | 1 | 1 | 0 | 0 | 5 | 4 |
| 0.5 | 0 | 0 | 0 | 0 | 3 | 5 | 4 | 5 |
| 1.0 | 0 | 0 | 2 | 3 | 0 | 0 | 7 | 6 |

TABLE 4

Activity of samples diluted in matching

| NaCl Conc. (M) | Minimum Surface Tension at 3 mg-TPL/ml (mN/m)(n = 3) | | | | | | | |
|---|---|---|---|---|---|---|---|---|
| | 10 mg/ml | | 20 mg/ml | | 30 mg/ml | | 30 mg/ml - Lyo | |
| | Avg | SD | Avg | SD | Avg | SD | Avg | SD |
| 0.13 | 0 | 0 | 1 | 1 | 0 | 0 | 5 | 4 |
| 0.5 | 0 | 1 | 5 | 5 | 10 | 4 | 0 | 0 |
| 1.0 | 7 | 4 | 12 | 1 | 11 | 3 | 7 | 7 |

Example 3

Measurement of Aerosol Output Rate of Surfactant-Salt Formulations

Each surfactant-salt solution was evaluated to determine its aerosol output rate. Aerosol output rate was measured using the Aeroneb Pro vibrating mesh nebulizer, and the Pari LC Star jet nebulizer. Samples were run through each nebulizer in triplicate. The results for the Aeroneb Pro nebulizer are presented in FIG. 1, and the results for the Pari LC Star nebulizer are presented in FIG. 2.

Aerosol output rate was measured at 10 mg/ml, 20 mg/ml, and 30 mg/ml. Aerosol output rate was greatest for the 10 mg/ml sample, with a slight decrease in output rate observed for the 20 mg/ml sample relative to the 10 mg/ml sample, and a further decrease in output rate observed for the 30 mg/ml sample relative to the 10 mg/ml and 20 mg/ml samples (FIG. 1). A slight decrease in aerosol output rate was observed upon increased salt concentration for the 10 mg/ml and 20 mg/ml samples (FIG. 1). In contrast, the 30 mg/ml sample demonstrated a relatively steady aerosol output rate with increasing salt concentration (FIG. 1).

Figure 2:
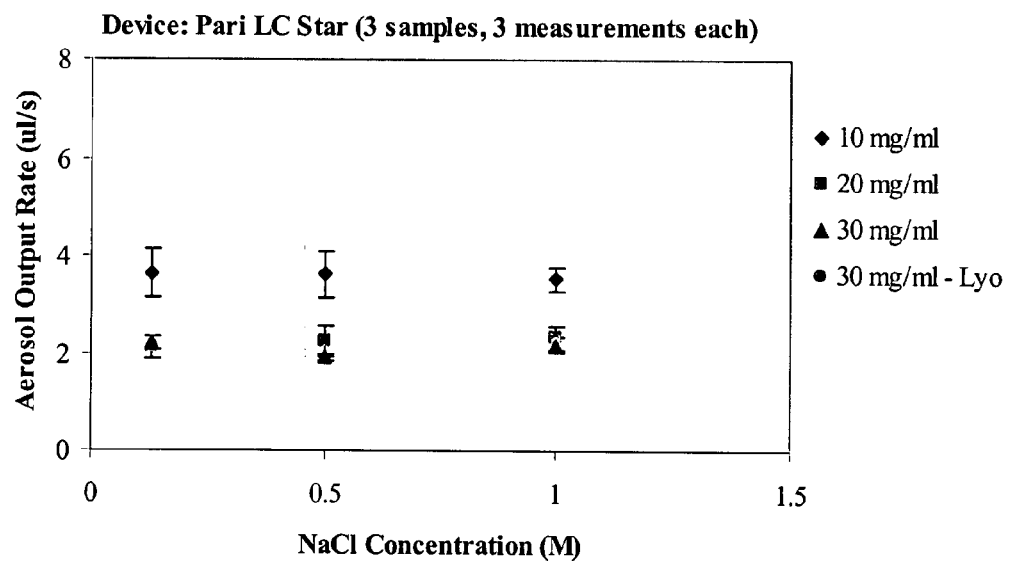
FIG. 2. Aerosol output rates (μl/sec) for lucinactant (10, 20, 30 mg/ml) or 30 mg/ml lyophilized KL4 surfactant formulations prepared with increasing concentrations of NaCl. Aerosol generator was Pari LC Star; data points represent three samples, three measurements each; error bars are indicated.

The output rate observed using the Pari LC Star nebulizer was less overall than the rate observed using the Aeroneb nebulizer, particularly with respect to the 10 mg/ml and 20 mg/ml samples. The output rate for the 10 mg/ml sample was greater than the 20 mg/ml and 30 mg/ml samples, and the 20 mg/ml and 30 mg/ml samples were observed to have nearly identical output rates at all salt concentrations tested (FIG. 2). No significant effect of increasing NaCl concentration on output rate was observed for any sample (FIG. 2). The eFlow device (Pari) employs a technology that is similar to the Aeroneb Pro, and output rates are comparable or slightly higher using the eFlow device.

Example 4

Evaluation of Clinical Efficacy of Coadministration of Hyperosmotic Agents and Pulmonary Surfactants This prophetic example describes how candidate combinations of hyperosmotic agents and surfactants as identified by the investigations described above can be evaluated for their efficacy in patients with pulmonary disorders.

To clinically assess the safety and efficacy of the inventive compositions and methods to treat pulmonary disorders, the following protocol is employed. The trials are structured as a double-blind, multi-location, randomized, vehicle-controlled, parallel group evaluation, and are conducted over the course of 2 to 12 weeks. The study compares different hyperosmotic agent-surfactant combinations with a placebo.

Upon selection to participate in the study, test subjects are evaluated on the following schedule: $FEV_1$ weekly, mucociliary clearance and Quality of Life measures at the beginning and end of the study.

Test subjects are randomly assigned to one of the following groups: (a) hyperosmotic agent plus surfactant; (b) placebo (in 0.9% isotonic saline). Each individual is treated for 4 weeks, three times daily with 3 ml of 20 mg/ml KL4 surfactant delivered by the Akita 2 aerosol generator. Device membranes are cleaned daily by sonication and handsets are replaced weekly.

The study assesses the following efficacy variables: (a) maintenance of pulmonary function, i.e., forced expiratory volume in one second ($FEV_1$) over time; (b) forced vital capacity (FVC); (c) rate of mucus clearance; (d) ratio of residual volume to total lung capacity (RV:TLC); (d) chest X-ray score; (e) validated Quality of Life measure (CFQoL); (f) occurrence or reduction in airway obstruction.

The present invention is not limited to the embodiments described and exemplified above, but is capable of variation and modification within the scope of the appended claims.

What is claimed:

1. A method for promoting mucus clearance in a patient with a pulmonary condition characterized by excessive mucus secretion or impaired mucus clearance, wherein the pulmonary condition is cystic fibrosis, bronchiectasis, primary or secondary ciliary diskinesia, COPD, or sinusitis, the method comprising administering to the patient at least one osmotically active agent and at least one synthetic pulmonary surfactant comprising one or more phospholipids and a synthetic polypeptide comprising at least 10 amino acid residues and no more than about 60 amino acid residues, said polypeptide including a sequence having alternating hydrophobic and hydrophilic amino acid residue regions represented by the formula $$(Z_aU_b)_cZd,$$

wherein:
Z is a hydrophilic amino acid residue independently selected from the group consisting of R and K;
U is a hydrophobic amino acid residue independently selected from the group consisting of L and C;
a is 1 or 2;
b has an average value of about 3 to about 8;
c is 1 to 10; and
d is 0 to 2,
wherein the synthetic polypeptide is admixed with the one or more phospholipids and wherein the at least one synthetic pulmonary surfactant has a surfactant activity greater than the surfactant activity of the one or more phospholipids alone, and wherein the at least one synthetic pulmonary surfactant is formulated to provide the patient with a lung dose of between about 20 and about 200 mg total phospholipid per day, thereby promoting the mucus clearance in the patient.

2. The method of claim 1, wherein the pulmonary surfactant comprises 1,2-dipalmitoyl-sn-glycero-3-phosphocholine (DPPC), 1-palmitoyl-2-oleoyl-sn-glycero-3-phosphoglycerol (POPG), palmitic acid (PA) and a peptide having a sequence of KLLLLKLLLLKLLLLKLLLLK (KL4, SEQ ID NO:1).

3. The method of claim 1, wherein the pulmonary surfactant is administered as a liquid instillate, a liquid aerosol or a dry aerosol.

4. The method of claim 1, wherein the lung dose is between about 30 and about 150 mg total phospholipid per day.

5. The method of claim 1, wherein the osmotically active agent is a pharmaceutically acceptable sugar, sugar alcohol or salt.

6. The method of claim 5, wherein the osmotically active agent is NaCl and is formulated as a saline solution.

7. The method of claim 6, wherein the saline solution comprises about 0.13 to about 1.2 Osm sodium chloride.

8. A method for promoting mucus clearance in a patient with cystic fibrosis, comprising administering to the patient at least one osmotically active agent and at least one synthetic pulmonary surfactant comprising one or more phospholipids and a synthetic polypeptide comprising at least 10 amino acid residues and no more than about 60 amino acid residues, said polypeptide including a sequence having alternating hydrophobic and hydrophilic amino acid residue regions represented by the formula $$(Z_aU_b)_cZd,$$

wherein:
Z is a hydrophilic amino acid residue independently selected from the group consisting of R and K;
U is a hydrophobic amino acid residue independently selected from the group consisting of L and C;
a is 1 or 2;
b has an average value of about 3 to about 8;
c is 1 to 10; and
d is 0 to 2,
wherein the synthetic polypeptide is admixed with the one or more phospholipids and wherein the at least one synthetic pulmonary surfactant has a surfactant activity greater than the surfactant activity of the one or more phospholipids alone, and wherein the at least one synthetic pulmonary surfactant is formulated to provide the patient with a lung dose of between about 20 and about 200 mg total phospholipid per day, thereby promoting the mucus clearance in the patient.

9. The method of claim 8, wherein the pulmonary surfactant comprises 1,2-dipalmitoyl-sn-glycero-3-phosphocholine (DPPC), 1-palmitoyl-2-oleoyl-sn-glycero-3-phosphoglycerol (POPG), palmitic acid (PA) and a peptide having a sequence of KLLLLKLLLLKLLLLKLLLLK (KL4, SEQ ID NO:1).

10. The method of claim 8, wherein the pulmonary surfactant is administered as a liquid instillate, a liquid aerosol or a dry aerosol.

11. The method of claim 8, wherein the lung dose is between about 30 and about 150 mg total phospholipid per day.

12. The method of claim 8, wherein the osmotically active agent is a pharmaceutically acceptable sugar, sugar alcohol or salt.

13. The method of claim 12, wherein the osmotically active agent is NaCl and is formulated as a saline solution.

14. The method of claim 13, wherein the saline solution comprises about 0.13 to about 1.2 Osm sodium chloride.

* * * * *